United States Patent [19]
Hill

[11] Patent Number: 5,837,651
[45] Date of Patent: Nov. 17, 1998

[54] SOLID FORMULATION

[75] Inventor: Alister Christie Hill, Kent, England

[73] Assignee: American Cyanamid Company, Madison, N.J.

[21] Appl. No.: 739,694

[22] Filed: Oct. 29, 1996

Related U.S. Application Data

[63] Continuation of Ser. No. 286,724, Aug. 5, 1994, Pat. No. 5,709,871.

[51] Int. Cl.$^6$ .................................................. A01N 33/26
[52] U.S. Cl. ........................................... 504/116; 424/405
[58] Field of Search ................................... 424/409, 405; 504/116

[56] References Cited

U.S. PATENT DOCUMENTS

| | | |
|---|---|---|
| 2,913,372 | 11/1959 | Velde et al. |
| 3,274,052 | 9/1966 | Yaffe et al. ............................... 424/421 |
| 4,289,525 | 9/1981 | Pasarela et al. ............................ 71/92 |
| 4,776,881 | 10/1988 | Mostafa et al. .......................... 504/283 |
| 5,372,989 | 12/1994 | Geigle et al. ............................ 504/116 |
| 5,474,971 | 12/1995 | Sandell ..................................... 504/116 |
| 5,491,160 | 2/1996 | Knight et al. ............................ 514/384 |

FOREIGN PATENT DOCUMENTS

| | | | |
|---|---|---|---|
| 0 501 798 A1 | 2/1992 | European Pat. Off. ....... | A01N 25/14 |
| 2 290 844 | 11/1975 | France ............................ | A01N 17/08 |
| 2 645 709 | 4/1990 | France ............................ | A01N 25/10 |
| 2645709 | 10/1990 | France . | |

OTHER PUBLICATIONS

Barker—May 1955 American Oil Chemists Society pp. 249–252.
Database WPI, Week 7237, Derwent Publications, Ltd., London, GB; AN 72–59251T [37] of JP-A-47 016 645 (Sumitomo Chemical) *abstract*.
Database WPI, Week 8351, Derwent Publications, Ltd., London, GB; AN 83–848783 [51] of SU-A-242 592 (UFA Plant Protect) Sep. 8, 1969 *abstract*.
Database WPI, Week 8450, Derwent Publications, Ltd., London, GB; AN 84–309677 [50] of JP-A-59 193 803 (Hoko Chem Ind) Nov. 2, 1984 *abstract*.
Database WPI, Week 8705, Derwent Publications, Ltd., London, GB; AN 87–033990 [05] of JP-A-61 291 501 (Kumiai Chem Ind) Dec. 22, 1986 *abstract*.
Database WPI, Week 8517, Derwent Publications, Ltd., London, GB; AN 85–102722 [17] of JP-A-60 048 904 (Kumiai Chem Ind) Mar. 16, 1985 *abstract*.

*Primary Examiner*—Peter F. Kulkosky
*Attorney, Agent, or Firm*—Charles F. Costello, Jr.

[57] ABSTRACT

A water dispersible solid formulation comprising an active ingredient, a surfactant of non-ionic type, a surfactant of anionic type and at least 30 wt % of urea is disclosed. A process of preparing the formulation and the use of the formulation for delivering an active ingredient, for example a pesticide or plant growth regulant to an agricultural or horticultural locus are also described.

15 Claims, 5 Drawing Sheets

SOLID FORMULATION

This is a continuation of application Ser. No. 08/286,724 filed on Aug. 5, 1994, now U.S. Pat. No. 5,709,871.

The present invention relates to a solid formulation and particularly, although not exclusively, relates to crop protection formulations which are in solid form, for example, powder, granules or tablets.

Crop protection agents are formulated in solid or liquid compositions, usually in the form of a concentrate for ease of handling and transportation, which are diluted with water by the user before application.

Since unsophisticated mixing techniques are often used for diluting solid formulations, one important requirement for such formulations is that of rapid dispersal in water. If a solid formulation does not disperse rapidly, clogging of spray equipment with undispersed formulation may occur and, furthermore, there may be inadequate application of active ingredient to the crop to be treated.

Many known processes for the preparation of solid crop protection formulations require the active ingredient to be pre-milled to a fine particle size and/or require a drying step, in order to remove water and form a solid. Such process steps add to the inefficiency of the overall process.

The patent literature discloses many solid crop protection formulations. For example, U.S. Pat. No. 3,274,052 (FMC) discloses a process for the preparation of pesticide granules which comprises the step of coating the surface of granular carrier particles with an active ingredient. The granular carrier particles may be any water-insoluble or water soluble, porous or non-porous material. Examples of water soluble materials disclosed include fertilisers such as ammonium phosphate, ammonium sulphate, urea, muriate of potash and super-phosphate.

French Patent Application No. 2 645 709 (Sumitomo) discloses a process for the preparation of an emulsifiable solid pesticidal composition which comprises melting a pesticide and a water soluble polymer, for example, polyethylene glycol, a surfactant, a solvent and/or a water soluble support. Examples of water soluble supports disclosed include hydropropylcellulose, urea, lactose and ammonium sulphate.

PCT Patent Application Number WO 91/13546 (DuPont) discloses water-dispersible or water-soluble pesticide granules which comprise 5% to 95% of pesticidal particles in combination with 5% to 40% of a water-soluble heat activated binder (HAB). Examples of HABs disclosed include ethylene oxide/propylene oxide copolymers and polyethoxylated dinonylphenol. The HABs may also include up to 50% co-binders such as polyethylene glycols, polyethylene oxide, polyethoxylated fatty acids or alcohols, hydrated inorganics such as sodium silicate, sorbital or urea.

Barker and Renauto disclosed urea adducts of non-ionic surface active agents in The Journal of the American Oil Chemist's Society, volume 32, May 1955 at page 249 et seq. The disclosure indicates that "other ingredients, such as perfumes, dyes, gums, alkaline builders, insecticides, germicides and solvents, may be added during the mixing or milling operation". It is believed that the mixture of urea adduct/insecticides proposed was a scatter formulation which was intended to be used in solid form.

This invention is based upon the discovery of a novel solid formulation which may rapidly be dispersed in water.

According to a first aspect of the present invention, there is provided a water dispersible solid formulation comprising:
an active ingredient;
a surfactant of a non-ionic type;
a surfactant of an anionic type; and
at least 30 wt % of urea.

Such a formulation has, surprisingly, been found to disperse rapidly in water.

In the context of this specification, the term "active ingredient" (or similar term) includes, within its scope, pesticides, for example, insecticides, fungicides, acaricides, ovicides, nematocides and herbicides, and plant growth regulators.

Said urea is preferably complexed with at least one of the other ingredients of the formulation. Said urea and at least one other ingredient are preferably in the form of an inclusion complex, for example a canal complex.

In an inclusion complex, two compounds are associated with one another such that one compound (hereinafter the "guest compound") is either wholly or partly locked within the crystal lattice of the other compound. In a canal complex, tunnels are defined by one compound, with the guest compound being wholly or partly located within the tunnels. In a canal complex of urea, the urea defines tunnels in which molecules of guest compound are located.

Preferably, urea is complexed with said surfactant of non-ionic type.

Said solid formulation may include at least 40 wt % of urea. Preferably, said solid formulation includes at least 45 wt % of urea. More preferably, said solid formulation includes at least 50 wt % of urea. Said solid formulation preferably includes no more than 70 wt % of urea.

Preferably, the ratio of urea to guest compound(s) is in the range 70:30 to 50:50.

Preferably, said urea is dispersed, suitably in a random fashion, throughout said solid formulation.

Said surfactant of non-ionic type preferably has predominantly non-ionic properties.

Said surfactant of non-ionic type is preferably an adjuvant. Such surfactants are normally available in the form of a mixture. Said surfactant of non-ionic type preferably predominantly includes aliphatic hydrocarbon moieties. Said aliphatic hydrocarbon moieties may be predominantly linear or branched. Preferably, linear hydrocarbon moieties predominate in said surfactant of non-ionic type.

In the context of this specification, the terms "predominate" and "predominantly" denote "more then 50 wt %" and, preferably, "more than 80 wt %".

Preferably, said surfactant of non-ionic type predominantly includes hydrocarbon moieties having at least 8 carbon atoms and, more preferably, having at least 10 carbon atoms. In the most preferred embodiment, said surfactant of non-ionic type predominantly includes hydrocarbon moieties having at least 12 carbon atoms.

The molecular weight of said surfactant of non-ionic type is preferably greater than 300 and, more preferably, within the range 350–20000.

Said surfactant of non-ionic type may be selected from alcohols (preferably fatty alcohols), esters (preferably fatty esters), and alkoxylated alcohols and esters.

Preferred surfactants of non-ionic type include polyethylene glycol, alkoxylated fatty alcohol and alkoxylated nonylphenol.

Where said surfactant of non-ionic type is alkoxylated, it is preferably ethoxylated and, preferably, includes on average less than 20, more preferably, less than 15, ethylene oxide units per molecule.

Said surfactant of non-ionic type preferably comprises at least 10 wt % of the solid formulation. Preferably said surfactant of non-ionic type comprises 10–40 wt %, more preferably 10–30 wt %, of the solid formulation.

Preferably, said surfactant of non-ionic type is of low hygroscopicity. At equilibrium, at 21° C. in air of 75% relative humidity, said surfactant of non-ionic type preferably takes up less than 25 g, more preferably, less than 20 g, of moisture per 100 g of the dry material. At equilibrium, at 21° C. in air of 32% relative humidity, said surfactant of non-ionic type preferably takes up less than 10 g, more preferably less than 5 g, of moisture per 100 g of the dry material.

Said surfactant of anionic type preferably has predominantly anionic properties. Preferred surfactants of anionic type include Morwet D425 (Trade Mark for a sodium salt of a sulphonated naphthalene/formaldehyde condensate), Empicol LZ (Trade Mark for sodium lauryl sulphate) and Nansa HS 85 (Trade Mark for sodium dodecylbenzene sulphonate).

Said surfactant of anionic type is preferably dispersed, suitably in a random fashion, throughout said solid formulation.

Preferably, said surfactant of anionic type comprises at least 4 wt % of the solid formulation. Preferably, said surfactant of anionic type comprises 4–30 wt %, more preferably 4–15 wt %, of the solid formulation. Preferably, the amount of surfactant of anionic type in said solid formulation is less than the amount of surfactant of non-ionic type in said formulation, weight for weight.

Preferably, said surfactant of anionic type is of low hygroscopicity. At equilibrium, at 21° C. in air of 75% relative humidity, said surfactant of anionic type preferably takes up less than 30 g, more preferably less than 25 g, of moisture per 100 g of the dry material. At equilibrium, at 21° C. in air of 32% relative humidity, said surfactant of anionic type preferably takes up less than 10 g, more preferably less than 5 g, of moisture per 100 g of the dry material.

Said active ingredient preferably comprises at least 5 wt % of the solid formulation. Preferably, said active pesticidal ingredient comprises 10–40 wt %, more preferably 10–20 wt %, of the solid formulation.

The melting point of said active ingredient may be at least 35° C. The melting point of said active ingredient is preferably in the range 35° C. to 95° C.

The solubility in water at 25° C. of said active ingredient may be less than 10,000 ppm and is preferably less than 1,000 ppm. The solubility in water at 25° C. of said active ingredient is preferably at least 1 ppm and is, more preferably, at least 10 ppm. It has, surprisingly, been found that a solid formulation which includes an active ingredient of low solubility in water does, in fact, disperse relatively rapidly in water.

A preferred active ingredient is triazamate [ethyl(3-tertbutyl-1-dimethylcarbamoyl-1H-1,2,4-triazol-5-ylthio) acetate]. It is believed that the following active ingredients may also advantageously be provided in a solid formulation in accordance with the present invention:

Alachlor (2-chloro-2',6'-diethyl-N-methoxymethylacetanilide), Aldicarb [2-methyl-2-(methylthio)propionaldehyde 0-methylcarbamoyloxime], Alpha-cypermethrin [a racemate comprising (S)-α-cyano-3-phenoxybenzyl (1R)-cis-3-(2,2-dichlorovinyl)-2,2-dimethylcyclopropanecarboxylate and (R)-α-cyano-3-phenoxybenzyl (1S)-cis-3-(2,2-dichlorovinyl)-2,2-dimethylcyclopropanecarboxylate], amitraz [N,N-bis(2,4-xyliminomethyl)methylamine], cymoxanil [1-(2-cyano-2-methyoxyiminoacetyl)-3-ethylurea], dimethomorph [4-[3-(4-chlorophenyl)-3-(3,4-dimethoxyphenyl)acryloyl]morpholine (Z to E ratio normally 4:1)], flamprop-M [Isopropyl N-benzoyl-N-(3-chloro-4-fluorophenyl)-D-alaninate and the corresponding methyl ester], flurenol-butyl [butyl ester of 9-hydroxyfluorene-9-carboxylic acid], flusilazole [bis(4-fluorophenyl)(methyl)(1H-1,2,4-triazol-1-ylmethyl) silane], pirimicarb [2-dimethylamino-5,6-dimethylpyrimidin-4-yl dimethylcarbamate], propoxur [2-isopropoxyphenyl methylcarbamate], and tetrachlorvinphos [(2)-2-chloro-1-(2,4,5-trichlorophenyl)vinyl dimethyl phosphate].

Said active ingredient is preferably dispersed, suitably in a random fashion, throughout said solid formulation.

The average particle size by volume of said active ingredient in said solid formulation may be less than 50 $\mu$m, is preferably less than 25 $\mu$m and, more preferably, is less than 10 $\mu$m.

The solid formulation may include one or a plurality of different active ingredients.

Said water dispersible solid formulation preferably includes less than 2 wt %, more preferably less than 1 wt %, of water.

Said water dispersible solid formulation may include a small amount of an acid, for example phosphoric acid or maleic acid. Preferably, said water dispersible solid formulation includes less than 5 wt % and, more preferably, less than 2 wt % of said acid.

Said water dispersible solid formulation may include a defoamer. In this case, less than 5 wt %, preferably less than 1 wt %, of said defoamer may be provided in the formulation.

Said water dispersible solid formulation may include up to 20 wt % of a finely divided mineral filler, for example gypsum, kaolinite, talc, bentonite, synthetic alumina silicates, colloidal alumina and colloidal silica.

Said water dispersible solid formulation may include a hydrocarbon which is preferably an adjuvant. Said hydrocarbon is preferably a straight chain hydrocarbon (preferably $C_{12}$ to $C_{24}$). Said hydrocarbon may comprise less than 20 wt %, preferably less than 15 wt % and, more preferably less than 10 wt % of the solid formulation. Where a hydrocarbon is provided, said surfactant of non-ionic type is preferably an emulsifier for the hydrocarbon when in water.

1 g of said water dispersible solid formulation preferably disperses fully in 100 ml of distilled water at 21° C. within 5 minutes, preferably within 2 minutes and, more preferably, within 1 minute.

According to a second aspect of the present invention, there is provided a process of preparing a water dispersible solid formulation of said first aspect, the process comprising mixing together an active ingredient, a surfactant of a non-ionic type, a surfactant of an anionic type and at least 30 wt % of urea and allowing the mixture to solidify.

The ingredients used in said process may be as described in any statement herein.

The process is preferably carried out under conditions which cause said urea to form an inclusion complex with one or more of the other ingredients.

Preferably, the active ingredient, the surfactant of non-ionic type and the surfactant of anionic type are mixed together, suitably at an elevated temperature, preferably in the range 30° C. to 90° C. A substantially homogenous mixture is preferably produced. Said urea is preferably then added to the mixture, suitably with mixing and at an elevated temperature, preferably within the range 30° C. to 90° C., more preferably within the range 30° C. to 45° C.

Preferably, in the process, one or more of the ingredients is caused to melt. Preferably, said surfactant of non-ionic type and/or said active ingredient is/are caused to melt. In a preferred embodiment, said active ingredient and said surfactant of non-ionic type are melted together with mixing at an elevated temperature, suitably to produce a substantially homogenous mixture. Said surfactant of anionic type is preferably then added with mixing, the mixture being maintained at an elevated temperature. The urea is preferably then added to the mixture, suitably with mixing. The mixture is then preferably allowed to cool to ambient temperature and allowed to stand for a period of time.

It has been found that, in the abovedescribed process, the active ingredient can form a fine solid particulate precipitate within the solid formulation.

In view of the steps in the abovedescribed process of initially melting the active ingredient and then allowing the active ingredient to precipitate, it may, advantageously., not be necessary to mill (or otherwise process) the active ingredient prior to the preparation of the solid formulation.

Preferably, the process is carried out in the presence of a minor amount of water. Water is suitably added in the process prior to the addition of urea.

It has been found that the amount of water present in the process affects the particle size of the active ingredient in the solid formulation and the dispersibility of the solid formulation. Preferably, the process is carried out in the presence of at least 1 wt % of water and, more preferably, in the presence of at least 2 wt % of water. Preferably, the process is carried out in the presence of less than 10 wt % of water and, more preferably, in the presence of less than 5 wt % of water.

Preferably, the process is carried out in the presence of a minor amount of an acid. Said acid is suitably added in the process prior to the addition of urea.

The product of the abovedescribed process is preferably dried or allowed to dry and may then be milled in order to produce a fine powder or formed into pellets or granules.

According to a third aspect of the present invention, there is provided a water dispersible solid formulation when prepared by the process of the second aspect.

According to a fourth aspect of the present invention, there is provided a method of delivering an active ingredient to a locus, the method comprising applying to the locus an aqueous dispersion of the water dispersible solid formulation of said first or said third aspects.

In the method, the locus may be an agricultural or horticultural locus.

Said method is preferably a method of combatting pests, for example aphid pests.

Said water dispersible solid formulation preferably comprises 0.1 to 50 g/kg, more preferably 0.25 to 20 g/kg of said aqueous dispersion.

According to a fifth aspect of the present invention, there is provided the use of a water dispersible solid formulation of said first or third aspects for the preparation of an aqueous dispersion for delivering an active ingredient to a locus.

Preferably, said locus is an agricultural or horticultural locus. Preferably, the use is for combatting pests.

The invention will now be described with reference to the following examples.

Examples 1 and 2 and Comparative Examples C1 and C2 show the effect on dispersibility of the solid formulations of including an anionic surfactant in the formulations.

Examples 3 to 6 and Comparative Example C3 illustrate the effect on dispersibility and active ingredient particle size of including an anionic surfactant in the formulations.

Examples 7 to 11 illustrate the effect on dispersibility of varying the quantity of water used in the processes of preparation of the formulations.

The chemicals described below are referred to in the Examples by a common name or trade name.

Triazamate (i.e. ethyl(3-tertbutyl-1-dimethylcarbamoyl-1H-1,2,4-triazol-5-ylthio) acetate)—sold under the Trade Mark AZTEC (outside U.S.A.) by Shell International Chemical Company Limited.—an aphicide.

Triton X-100 (Trade Mark)—octylphenol ethoxylate with 9–10 ethylene oxide units, supplied by Rohm & Haas—a non-ionic adjuvant.

Morwet D425 (Trade Mark)—a sodium salt of a sulphonated naphthalene/formaldehyde condensate, supplied by Witco—an anionic surfactant.

PEG 6000 and PEG 400—polyethylene glycol of average molecular weight of 6000 and 400 respectively—a non-ionic adjuvant.

Hoe S4004 (Trade Mark)—a natural alcohol ethoxylate containing 7 ethylene oxide units, supplied by Hoechst—a non-ionic adjuvant.

Genapol C100 (Trade Mark)—a coconut alcohol having 10 ethylene oxide units, supplied by Hoechst—a non-ionic adjuvant.

Arkopal N110 (Trade Mark)—a nonylphenol ethoxylate with 11 ethylene oxide units—a non-ionic surfactant.

Nansa HS 85 ( Trade Mark)—sodium dodecylbenzene sulphonate, supplied by Albright and Wilson—an anionic surfactant.

Empicol LZ (Trade Mark)—sodium lauryl sulphate, supplied by Albright and Wilson—an anionic surfactant.

The ingredients of the formulations of Examples 1, 2 and Comparative Examples C1, C2 are shown in Table 1. Details on the processes for the preparation of the formulation of the Examples are provided below. Example 1, 2, C1 and C2 were each prepared on a 50 g scale.

EXAMPLE 1

Triazamate and Triton X-100 were weighed into a suitable screw-capped jar in a fume cupboard. The jar was then capped and stored in a laboratory oven at 70° to 80° C. with swirling until the triazamate and Triton X-100 had melted together to form a mixture. Morwet D425 was then added and heated with the mixture for between 20 and 30 minutes. The mixture was then stirred thoroughly. Subsequently, urea was added to the mixture at ambient temperature.

Observations

After addition of urea, the mixture was a viscous dark brown paste. After 75 minutes standing at ambient temperature, the mixture became hard but not brittle. After 16 hours standing, the mixture became a hard, sticky, unstirrable paste.

EXAMPLE 2

The process of Example 1 was followed, with phenylsulphonate being added instead of Morwet D425.

Observations

After addition of urea, a viscous, but easily stirrable, paste resulted which had not hardened after 75 minutes standing at ambient temperature. After standing at ambient temperature overnight, the mixture remained as a softish greasy gel.

COMPARATIVE EXAMPLE C1

Triazamate was added to a hot solution of PEG 6000 in Triton X-100 and dissolved by heating and swirling. The urea (at ambient temperature) was then stirred into the solution without delay.

Observations

The mixture was relatively viscous after standing for about one minute at ambient temperature. After standing overnight, the mixture became hard, but not brittle.

COMPARATIVE EXAMPLE C2

Triazamate and Triton X-100 were melted together at 60° to 65° C. to form a mixture. The urea (at ambient temperature) was added without delay and with stirring.

Observations

After 90 minutes standing at ambient temperature the mixture was a viscous paste. After standing overnight, the mixture became a waxy, non-comminutable gel.

closed jar was placed in an oven at 60°–70° C. After 35–45 minutes standing, the mixture was allowed to cool with stirring to 40°–42° C. Temperature was monitored continuously using a Eurisem Technics (Trade Mark) electronic thermometer fitted with a "K" Type 622 (Trade Mark) probe. The jar was then opened and the urea added and incorporated into the mixture without delay by stirring for a few minutes with a metal spatula or rod. The jar was then closed and allowed to stand at ambient temperature for at least 16 hours. During this period, the triazamate was precipitated in a solid particulate form.

The products of the above process which were generally fudge-like masses were transferred to open dishes or trays in which they were allowed to dry to constant weight at ambient temperature either in a vacuum oven, or in a fume cupboard. The dried masses thus obtained were, if hard

TABLE 1

| EXAMPLE NO. | WEIGHT % ADDED | | | | | |
|---|---|---|---|---|---|---|
| | Triaxamate | TRITON X-100 | MORWET D425 | PHENYL-SULPHONATE Ca | PEG 6000 | UREA |
| 1 | 14.6 | 14.0 | 14.0 | — | — | 57.4 |
| 2 | 14.6 | 28.6 | — | 4.0 | — | 52.8 |
| C1 | 14.8 | 15.0 | — | — | 14.0 | 56.2 |
| C2 | 14.6 | 28.6 | — | — | — | 56.8 |

EXAMPLES 3 TO 6 AND COMPARATIVE EXAMPLE C3

The ingredients of the formulations of Examples 3 to 6 and Comparative Example C3 are shown in Table 2. Each formulation was prepared according to the general process described below.

Triazamate and Hoe S4004 were weighed into a suitable screw-capped jar (60–500 g capacity) in a fume cupboard. The jar was capped and then stored in a laboratory oven at 65° to 75° C. until the triazamate and Hoe S4004 had melted. Subsequently, the melt was stirred or swirled gently in the jar to homogenise it. With the jar placed on a pan of an electronic balance, all other ingredients of the formulation (with the exception of urea) were then weighed in immediately. The most usual order of addition was (1) phosphoric acid; (2) Morwet D425 (if added); and (3) water. After mixing the ingredients, as far as possible, by swirling, the enough, converted to a coarse powder by milling for 5 to 10 seconds in a small coffee mill which was operated in a fume cupboard. The powder formed was then screened on a BS16 mesh sieve (1 mm apertures). Any oversize powder was re-milled until it could pass the same sieve.

TABLE 2

| EXAMPLE NO. | WEIGHT % ADDED | | | | | |
|---|---|---|---|---|---|---|
| | Triaxamate | Hoe S4004 | MORWET D425 | PHOS-PHORIC ACID | WATER | UREA |
| 3 | 14.0 | 24.0 | 4.0 | 0.5 | 3.0 | 54.5 |
| 4 | 14.0 | 21.0 | 7.0 | 0.5 | 3.0 | 54.5 |
| 5 | 14.0 | 18.0 | 10.0 | 0.5 | 3.0 | 54.5 |
| 6 | 14.0 | 15.0 | 13.0 | 0.5 | 3.0 | 54.5 |
| C3 | 14.0 | 28.0 | — | 0.5 | 3.0 | 54.5 |

EXAMPLE 7

By processes analogous to those described above, various formulations were prepared using the following ingredients:

| Ingredient | Weight % added |
|---|---|
| Triazamate | 14.0 |
| PEG 400 | 14.0 |
| Morwet D425 | 13.0 |
| Water | 0–10 |
| Urea | balance up to 100 |

It will be appreciated that, in this example, the weight percent of triazamate, PEG 400 and Morwet D425 added to the various formulations remains constant, but the weight percent of water added in the process is varied, with urea making up the balance.

EXAMPLE 8

By processes analogous to those described above, various formulations were prepared using the following ingredients:

| Ingredient | Weight % added |
| --- | --- |
| Triazamate | 14.0 |
| Genapol C100 | 14.0 |
| Morwet D425 | 13.0 |
| Phosphoric acid | 0.5 |
| Water | 0–6.00 |
| Urea | balance up to 100 |

As in Example 7, the weight percent of water added is varied, with urea making up the balance.

EXAMPLE 9

By processes analogous to those described above, various formulations were prepared using the following ingredients:

| Ingredient | Weight % added |
| --- | --- |
| Triazamate | 14.0 |
| Arkopal N110 | 14.0 |
| Morwet D425 | 13.0 |
| Water | 0 to 4.0 |
| Phosphoric acid | 0.5 |
| Urea | balance up to 100 |

As in Example 7, the weight percent of water added is varied, with urea making up the balance.

EXAMPLE 10

By processes analogous to those described above, various formulations were prepared using the following ingredients:

| Ingredient | Weight % added |
| --- | --- |
| Triazamate | 14.0 |
| Genapol C100 | 14.0 |
| Nansa HS 85 | 13.0 |
| Phosphoric acid | 0.25 |
| Water | 0 to 3.0 |
| Urea | balance up to 100 |

As in Example 7, the weight percent of water added is varied, with urea making up the balance.

EXAMPLE 11

By processes analogous to those described above, various formulations were prepared using the following ingredients:

| Ingredient | Weight % added |
| --- | --- |
| Triazamate | 14.0 |
| Hoe S4004 | 14.0 |
| Empicol LZ | 13.0 |
| Maleic acid | 0.2 |
| Defoamer SF | 1.0 |
| Water | 0–2.0 |
| Urea | balance up to 100 |

As in Example 7, the weight percent of water added is varied, with urea making up the balance. (It should be noted that Defoamer SF itself includes 93% water).

EXAMPLE 12

Dispersibility of the Formulations in Water

Dispersibility of the formulations of Examples 1 to 11 and Comparative Examples C1 to C3 was examined in a simple procedure which involved the addition of 100 ml of distilled water to 1.00 g of the formulations in a 250 ml beaker followed by occasional gentle swirling. No particular care was taken with the form, e.g. coarse or fine, in which the formulations were added to the water, unless otherwise stated.

Details concerning the dispersibility of the formulations are noted in Table 3 below.

TABLE 3

| EXAMPLE NO: | DISPERSIBILITY |
| --- | --- |
| 1 | Lumps up to 8 mm in size dispersed completely within 9 minutes |
| 2 | Lumps up to 8 mm in size dispersed completely within 24 to 25 minutes |
| 3 | Granules up to 1 mm in size dispersed completely within 1.5 to 2 minutes |
| 4 | Granules up to 1 mm in size dispersed completely within 60 to 70 seconds |
| 5 | Granules up to 1 mm in size dispersed completely within 45 to 60 seconds |
| 6 | Granules up to 1 mm in size dispersed completely within 45 seconds |
| 7 | Lumps up to 8 mm in size dispersed in circa 3 minutes when prepared using greater than 2.5% water |
| 8 | Lumps up to 8 mm in size dispersed completely in less than 11 minutes when prepared using greater than 2.5% water |
| 9 | Lumps up to 8 mm in size dispersed in less than 5 minutes when prepared using greater than 2.5% water |
| 10 | Lumps up to 8 mm in size dispersed in less than 11 minutes when prepared using greater than 2.5% water |
| 11 | Lumps up to 8 mm in size dispersed in less than 8 minutes when prepared using greater than 1.0% water |
| C1 | Lumps up to 8 mm in size dispersed only partially |

TABLE 3-continued

| EXAMPLE NO: | DISPERSIBILITY |
|---|---|
| | within 60 minutes |
| C2 | Lumps up to 8 mm in size did not disperse completely within 60 minutes |
| | Granules up to 1 mm in size took >20 minutes for dispersion |

EXAMPLE 13

Particle Size Analysis of the Formulations

A particle size analysis of the formulations of Examples 3 to 11 and Comparative Example C3 was carried out using a Sympatec Helos laser diffraction instrument operated according to the maker's instructions.

All measurements were carried out using, as measuring medium, distilled water that had been pre-saturated with triazamate at the test room temperature and then filtered through a 0.2 $\mu$m cellulose nitrate membrane prior to use.

Details concerning the average triazamate particle size for Examples 3 to 6 and Comparative Example C3 are provided in Table 4 below.

TABLE 4

| EXAMPLE NO. | Average triazamate particle size/$\mu$m |
|---|---|
| 3 | 15.6 |
| 4 | 11.0 |
| 5 | 8.0 |
| 6 | 5.9 |
| C3 | 19.6 |

Figure 1:
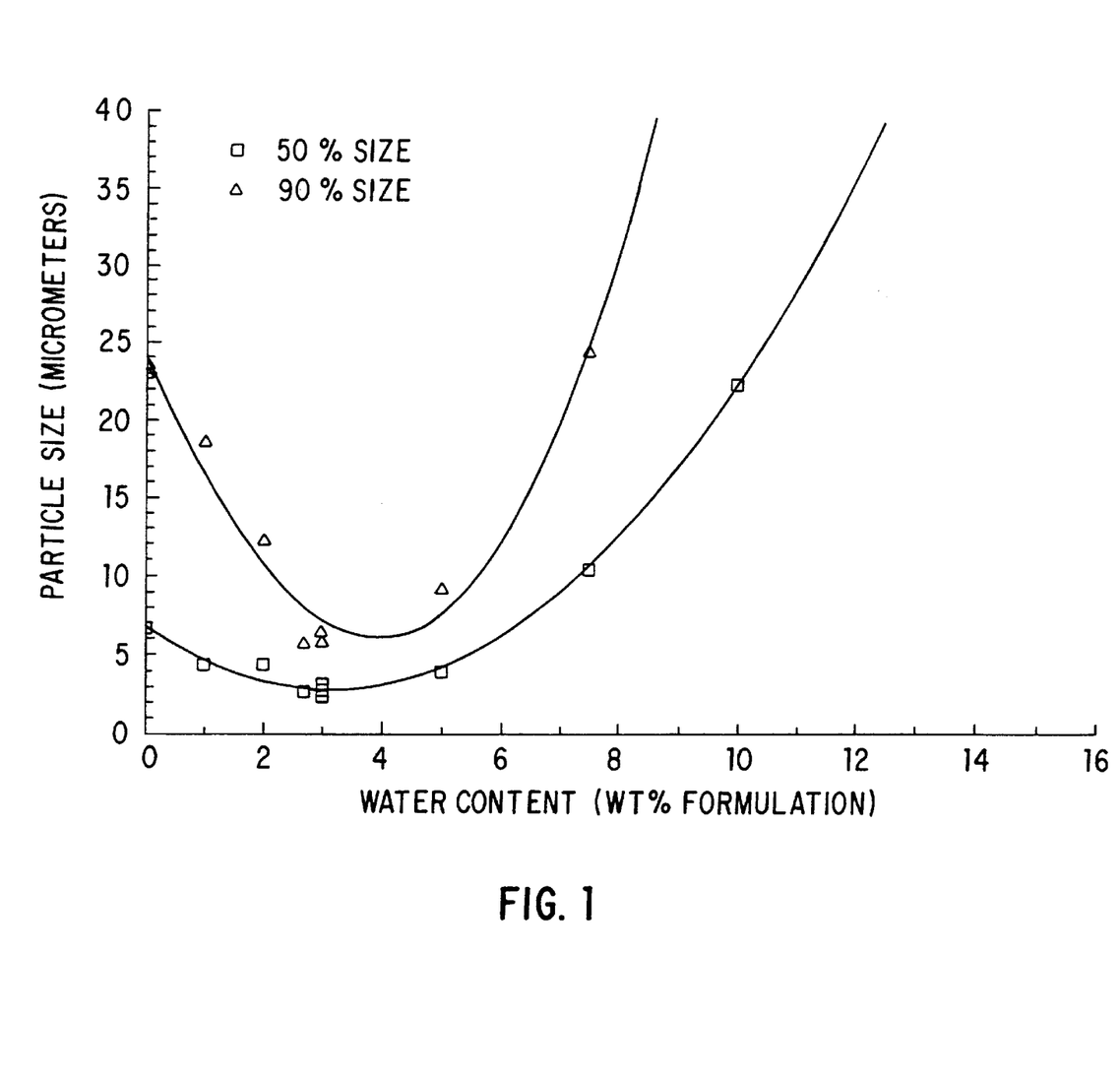
FIGS. 1 to 5 graphically show the particle size in the ordinate, as a function of the water content in the abscissa, respectively for the formulations in Examples 7 to 11.
Figure 2:
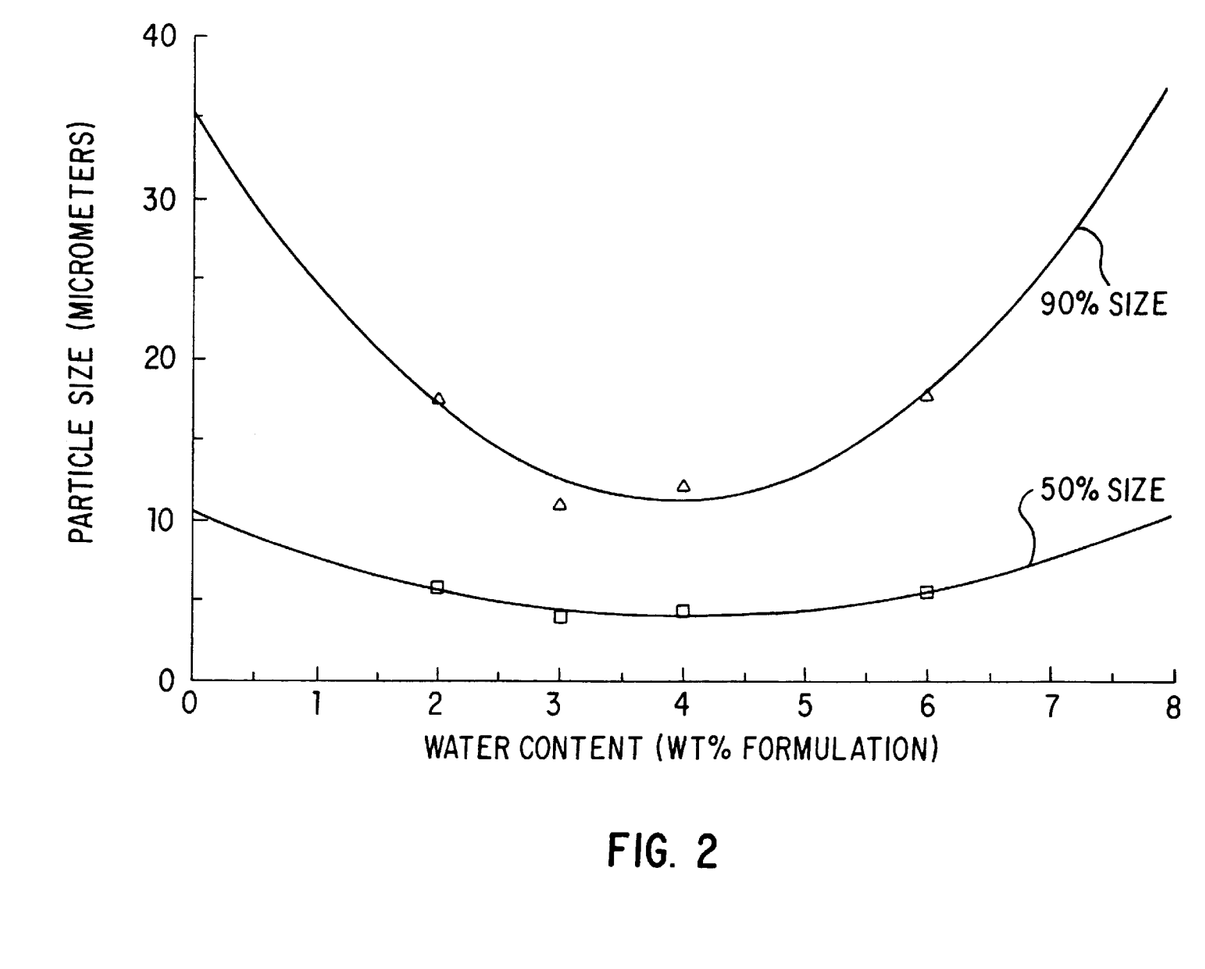
Figure 3:
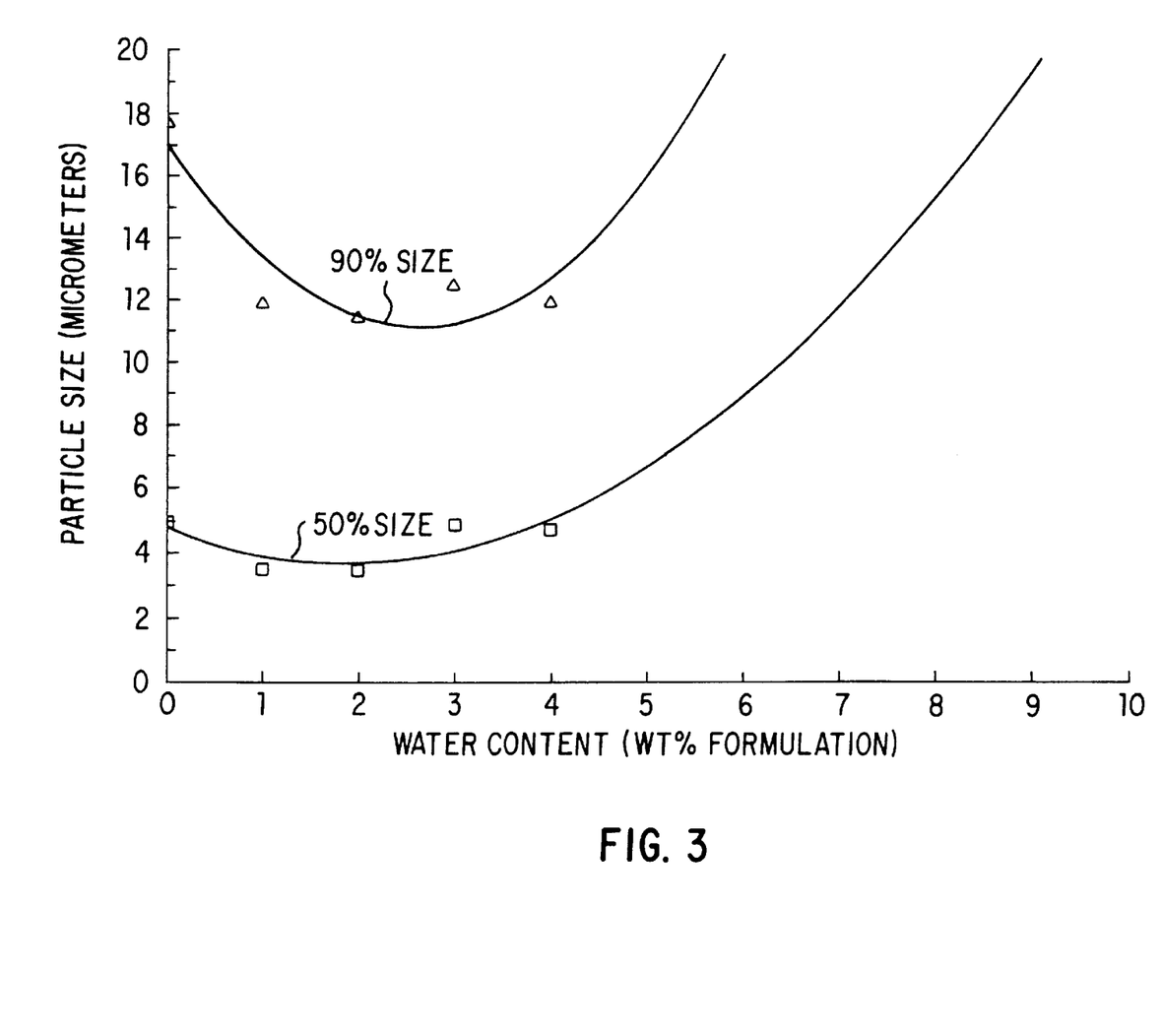
Figure 4:
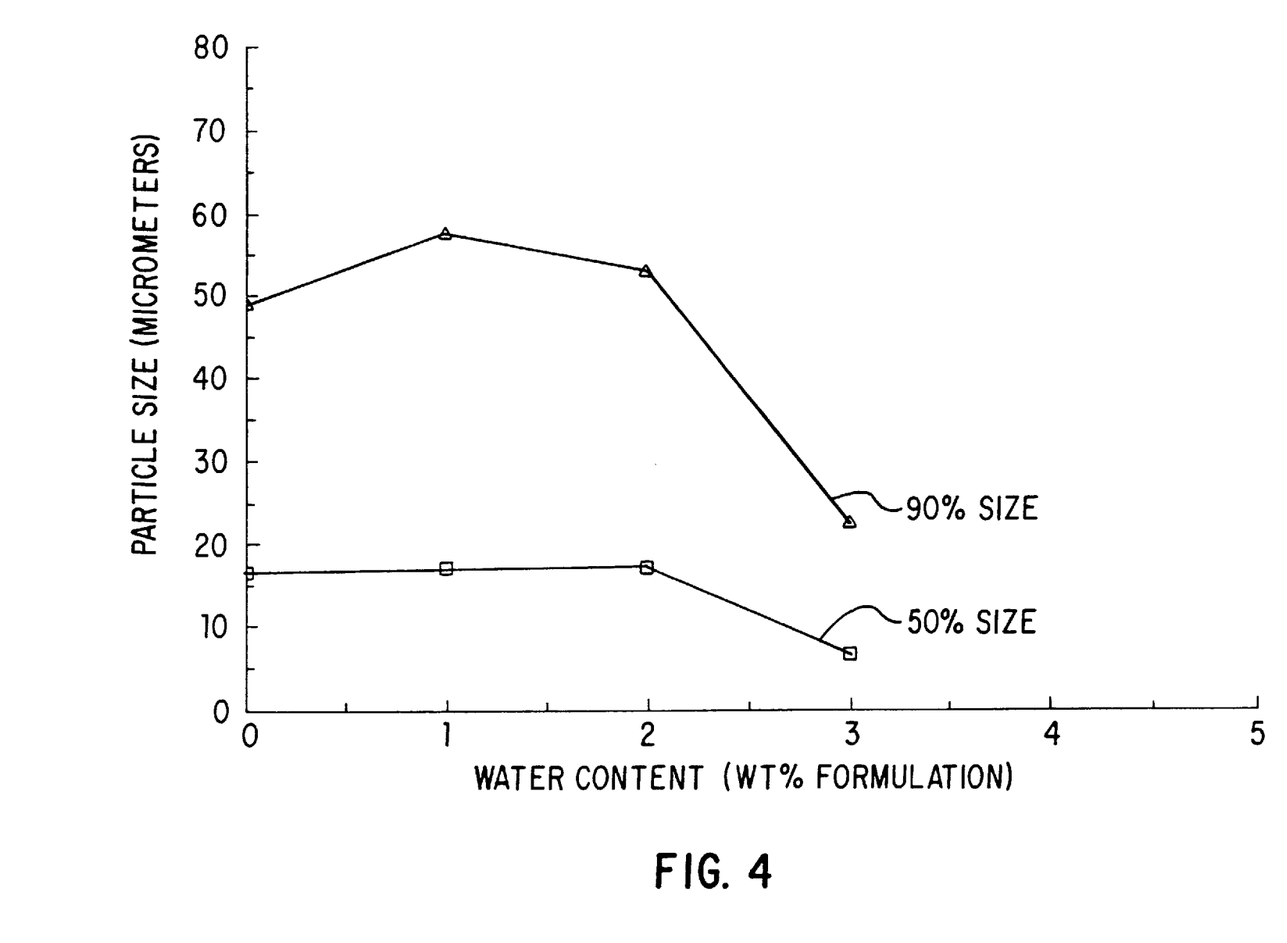
Figure 5:
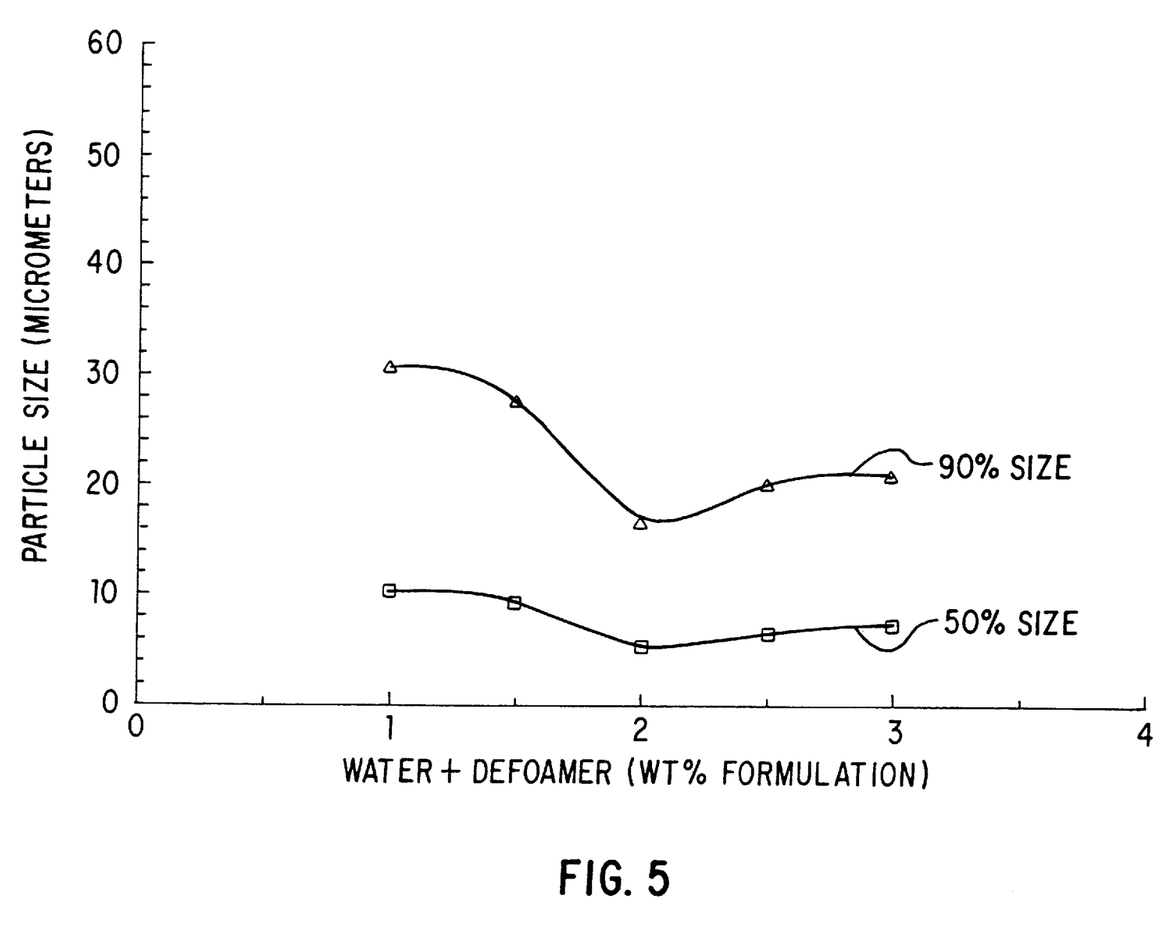

For Examples 7 to 11, the results are presented in graphical form, as follows:

| Example | Figure No. |
|---|---|
| 7 | see FIG. 1 |
| 8 | see FIG. 2 |
| 9 | see FIG. 3 |
| 10 | see FIG. 4 |
| 11 | see FIG. 5 |

The graphs of FIGS. 1 to 5 were generated using a graphics software package sold under the Trade Mark "T-curve" which was available on a Sperry Type 3126-00 (Trade Mark) computer. The curves shown are "best fits".

In each of FIGS. 1 to 5, two curves are shown which represent maximum particle size of the smallest 50% and 90% of particles respectively.

The following points may be concluded from the Examples discussed above:

(i) The speed of dispersibility of the formulations in water is increased when an anionic surfactant (e.g. Morwet D425 or Phenylsulphonate Ca) is used in the formulations—Compare Examples 1 and 2 with Examples C1 and C2; and compare Examples 3 to 6 with Example C3.

(ii) The speed of dispersibility of the formulations in water is increased the greater the amount of anionic surfactant used in the formulations—Compare Examples 3 to 6 which show the effect of increasing the amount of anionic surfactant (Morwet D425) in the formulations.

(iii) The average size of active ingredient (e.g. triazamate) particles in the dispersed formulations decreases as the amount of anionic surfactant in the formulations increases—Compare Examples 3 to 6.

(iv) The fineness of the precipitated triazamate particles and, hence, the speed of dispersibility of the formulations in water, is affected by the quantity of water used in the processes of preparation of the formulations—see Examples 7 to 11 and FIGS. 1 to 5.

The following effects have also been noted:

(v) The use of an anionic surfactant in the process for the preparation of the formulations aids the solidification of the formulations.

(vi) The shape of the precipitated particles of active ingredient (e.g. triazamate) is dependent upon the nature of non-ionic surfactant used.

(vii) When the water dispersed formulations are used in the treatment of pests, the effect against pests is comparable to equivalent emulsion concentrates and/or suspension concentrates of the active ingredients.

I claim:

1. A water dispersible solid formulation comprising an active ingredient selected from the group consisting of alachlor, aldicarb, alpha-cypermethrin, amitraz, cymoxanil, dimethomorph, flamprop-M, flurenol-butyl, flusilazole, pirimicarb, propoxur, tetrachlorvinphos, and a mixture thereof, the active ingredient having an average particle size by volume of less than about 50 $\mu$m;

at least about 10 wt % of a surfactant of non-ionic type selected from the group consisting of an alcohol and an ester;

at least about 4 wt % of a surfactant of an anionic type;

at least about 1 wt % of water; and at least 30 wt % of urea whereby, when the water dispersible solid formulation is added to water, the average particle size of the active ingredient can decrease as the amount of the surfactant of the anionic type increases.

2. A water dispersible solid formulation comprising:

a melt having an effective amount of an active ingredient selected from the group consisting of alachlor, aldicarb, alpha-cypermethrin, amitraz, cymoxanil, dimethomorph, flamprop-M, flurenol-butyl, flusilazole, primicarb, propoxur, tetrachlorvinphos, and a mixture thereof, the active ingredient having an average particle size by volume of less than 50 $\mu$m, and at least about 10 wt % of a surfactant of a non-ionic type selected from the group consisting of and alcohol and ester;

at least about 4 wt % of a surfactant of an anionic type;

at least about 1 wt % of water; and at least 30 wt % of urea whereby, when the water dispersible solid formulation is added to water, the average particle size of the active ingredient can decrease as the amount of the surfactant of the anionic type increases.

3. A water dispersible solid formulation comprising:

an active pesticide ingredient having an average particle size by volume of less than about 25 $\mu$m;

at least about 10 wt % of a non-ionic surfactant selected from the group consisting of an alcohol and ester;

at least about 4 wt % of an anionic surfactant;

at least about 1 wt % of water; and at least 30 wt % of urea, with the proviso that the melting point of the active ingredient is less than the decomposition temperature of the non-ionic and anionic surfactant and whereby, when the water dispersible solid formulation is added to water, the average particle size of the active ingredient can decrease as the amount of the anionic surfactant increases.

4. A formulation as claimed in claim 1 or 2 or 3, wherein said urea is complexed with said surfactant of non-ionic type.

5. A formulation as claimed in claim 1 or 2 or 3, including at least 50 wt % of urea.

6. A formulation as claimed in claim 4, including 10–40 wt % of said surfactant of non-ionic type.

7. A formulation as claimed in claim 1 or 2 or 3, including 4–30 wt % of said surfactant of anionic type.

8. A formulation as claimed in claim 1 or 2 or 3, including 10–40 wt % of said active ingredient.

9. A process of preparing a water dispersible solid formulation according to claim 1 or 2 or 3, the process comprising mixing together a melt consisting essentially of an active ingredient and at least about 10 wt % of a surfactant of a non-ionic type, at least about 4 wt % of a surfactant of an anionic type, at least about 1 wt % of water and at least about 10 wt % of urea to obtain a mixture, and allowing the mixture to solidify.

10. A process as claimed in claim 7, wherein the process is carried out in the presence of less than about 10 wt % of water.

11. A method of applying an active ingredient to a locus, the method comprising applying to the locus an aqueous dispersion of a water dispersible solid formulation as claimed in claim 1 or 2 or 3.

12. A formulation of claim 3 wherein said active pesticide ingredient is selected from the group consisting of triazamate, aldicarb, amitraz, cymoxanil, dimethomorph, flamprop-M and the corresponding methyl ester of flamprop-M, flurenol-butyl, flusilazole, pirimicarb, tetrachlorvinphos, and a mixture thereof.

13. A formulation of claim 1 or 2 or 3 with the future proviso that the active pesticide ingredient is not alachlor, alpha-cypermethrin or propoxur.

14. A formulation of claim 12, wherein said active pesticide ingredient has an average particle size of less than about 10 μm.

15. A formulation of claim 13, wherein said active pesticide ingredient has an average size of less than about 10 μm.

* * * * *